United States Patent
Yamazaki

(10) Patent No.: US 11,624,721 B2
(45) Date of Patent: Apr. 11, 2023

(54) HYDROGEN SENSOR, HYDROGEN DETECTING METHOD, AND NON-TRANSITORY COMPUTER-READABLE STORAGE MEDIUM

(71) Applicant: KABUSHIKI KAISHA TOSHIBA, Tokyo (JP)

(72) Inventor: Hiroaki Yamazaki, Yokohama (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 993 days.

(21) Appl. No.: 16/352,440

(22) Filed: Mar. 13, 2019

(65) Prior Publication Data

US 2020/0080954 A1 Mar. 12, 2020

(30) Foreign Application Priority Data

Sep. 10, 2018 (JP) .............................. JP2018-168890

(51) Int. Cl.
*G01N 27/12* (2006.01)
*B81B 7/02* (2006.01)

(52) U.S. Cl.
CPC ............. *G01N 27/128* (2013.01); *B81B 7/02* (2013.01); *G01N 27/123* (2013.01); *B81B 2201/0292* (2013.01)

(58) Field of Classification Search
CPC .. G01N 27/128; G01N 27/123; G01N 33/005; G01N 27/227; B81B 7/02; B81B 2201/0292
USPC ....................................................... 73/31.06
See application file for complete search history.

(56) References Cited

U.S. PATENT DOCUMENTS

| | | | | |
|---|---|---|---|---|
| 6,539,774 B1* | 4/2003 | Zinck | ..................... | H01M 10/48 436/144 |
| 7,340,941 B1* | 3/2008 | Fruhberger | .......... | G01N 29/036 73/24.01 |
| 2005/0186117 A1* | 8/2005 | Uchiyama | ............ | G01N 21/783 436/164 |
| 2008/0038590 A1* | 2/2008 | Nakakubo | .............. | G01N 27/16 429/468 |
| 2011/0259083 A1* | 10/2011 | Lee | ...................... | G01N 33/005 427/125 |

(Continued)

FOREIGN PATENT DOCUMENTS

| CN | 106370706 A | * | 2/2017 | ........... G01N 27/227 |
|---|---|---|---|---|
| JP | 2016-170161 A | | 9/2016 | |

(Continued)

*Primary Examiner* — Marrit Eyassu
(74) *Attorney, Agent, or Firm* — Oblon, McClelland, Maier & Neustadt, L.L.P.

(57) ABSTRACT

According to one embodiment, a hydrogen sensor is disclosed. The hydrogen sensor includes a capacitor, a gas detector, a heater, and a determiner. The capacitor includes a deformable member that deforms by absorbing or adsorbing hydrogen and varies a capacitance value corresponding to a deformation of the deformable member. The gas detector detects gas based on a capacitance value of the capacitor. The heater heats the deformable member. The determiner determines whether gas detected by the gas detector contains a substance other than hydrogen or not, wherein the gas detector detects the gas during a heating period during which the heater heats the deformable member.

19 Claims, 12 Drawing Sheets

(56) References Cited

U.S. PATENT DOCUMENTS

2012/0032692 A1\* 2/2012 Kothari ............... G01N 27/227
              324/672
2017/0343522 A1   11/2017 Ikehashi et al.
2019/0086377 A1    3/2019 Ikehashi et al.

FOREIGN PATENT DOCUMENTS

JP  2017-215170 A  12/2017
JP   2019-56607 A   4/2019

\* cited by examiner

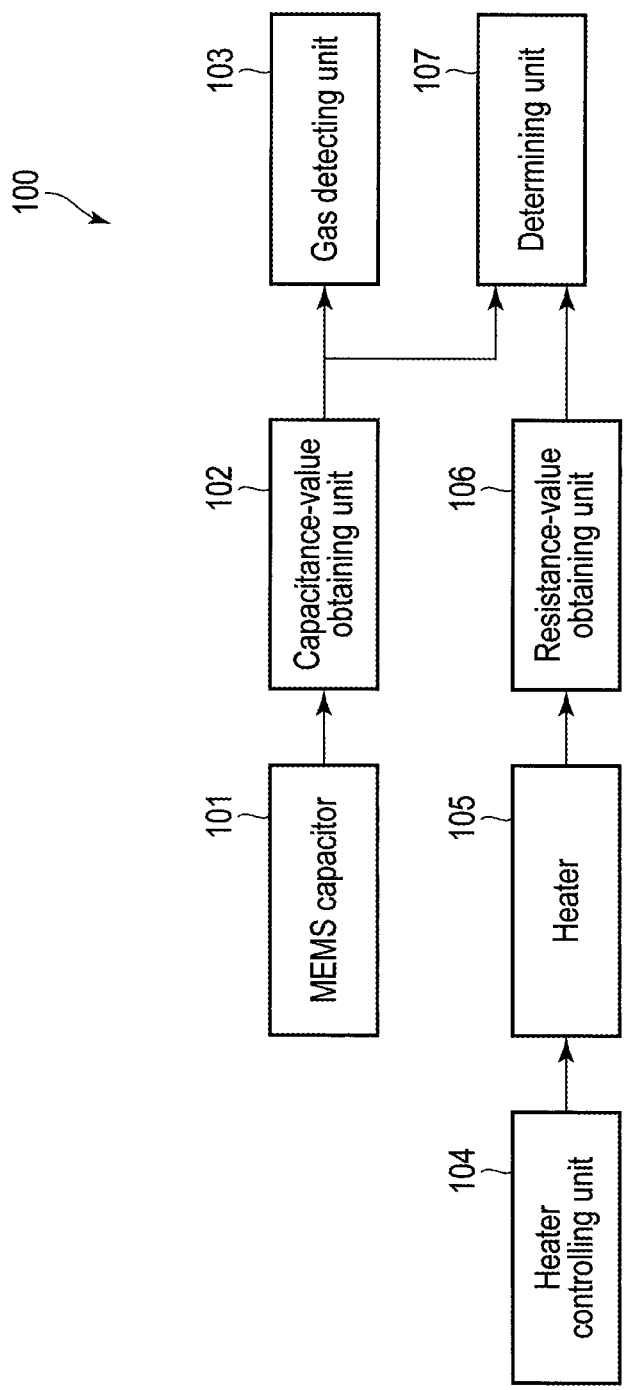
F I G. 1

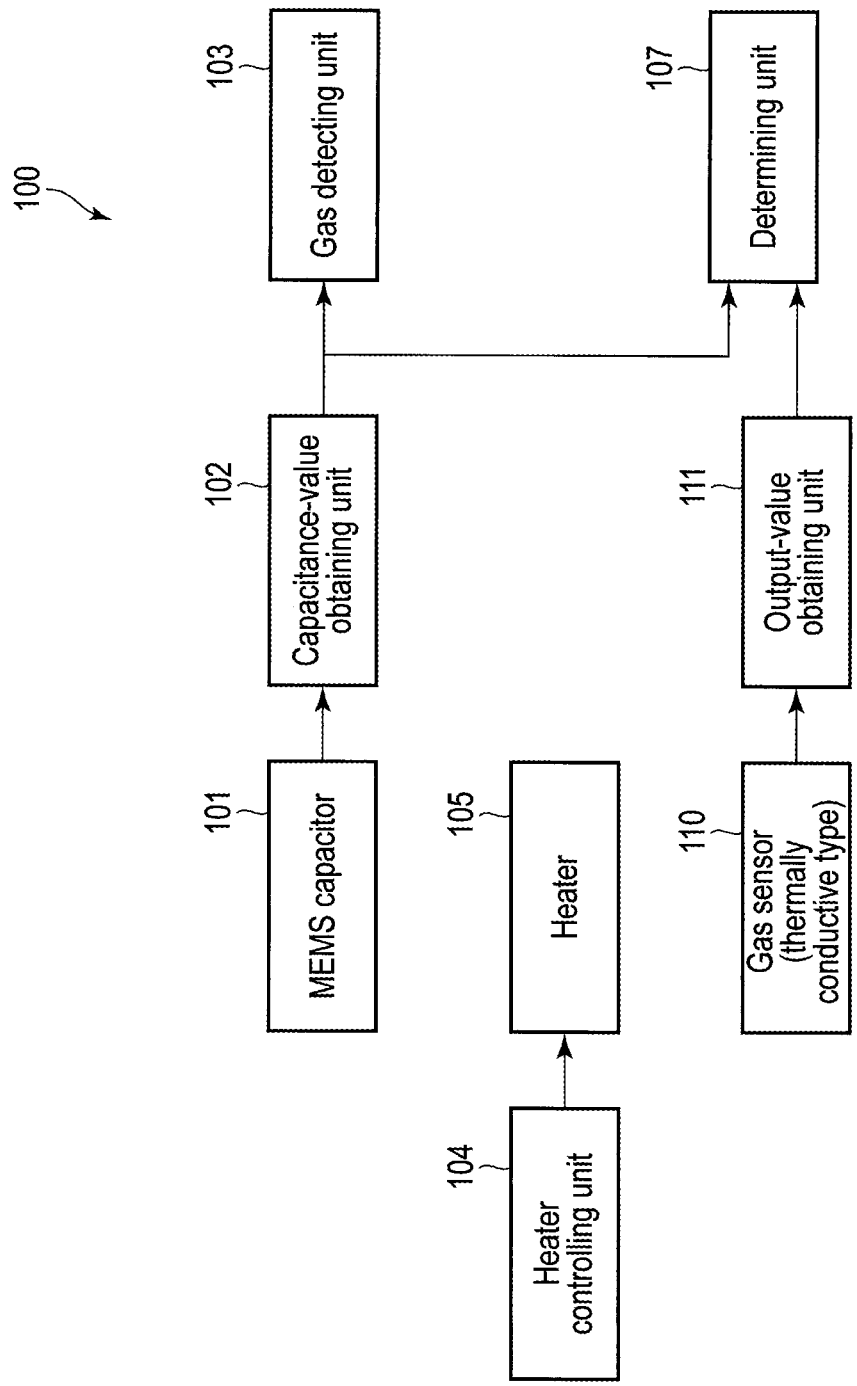
F I G. 6

| Gas species | ΔC | ΔR | ΔV |
|---|---|---|---|
| Hydrogen ($H_2$) | + | − | + |
| Methane ($CH_4$) | − | − | + |
| Propane ($C_3H_8$) | + | + | + |
| $CO_2$ | + | + | 0 |
| He | − | − | 0 |

F I G. 10

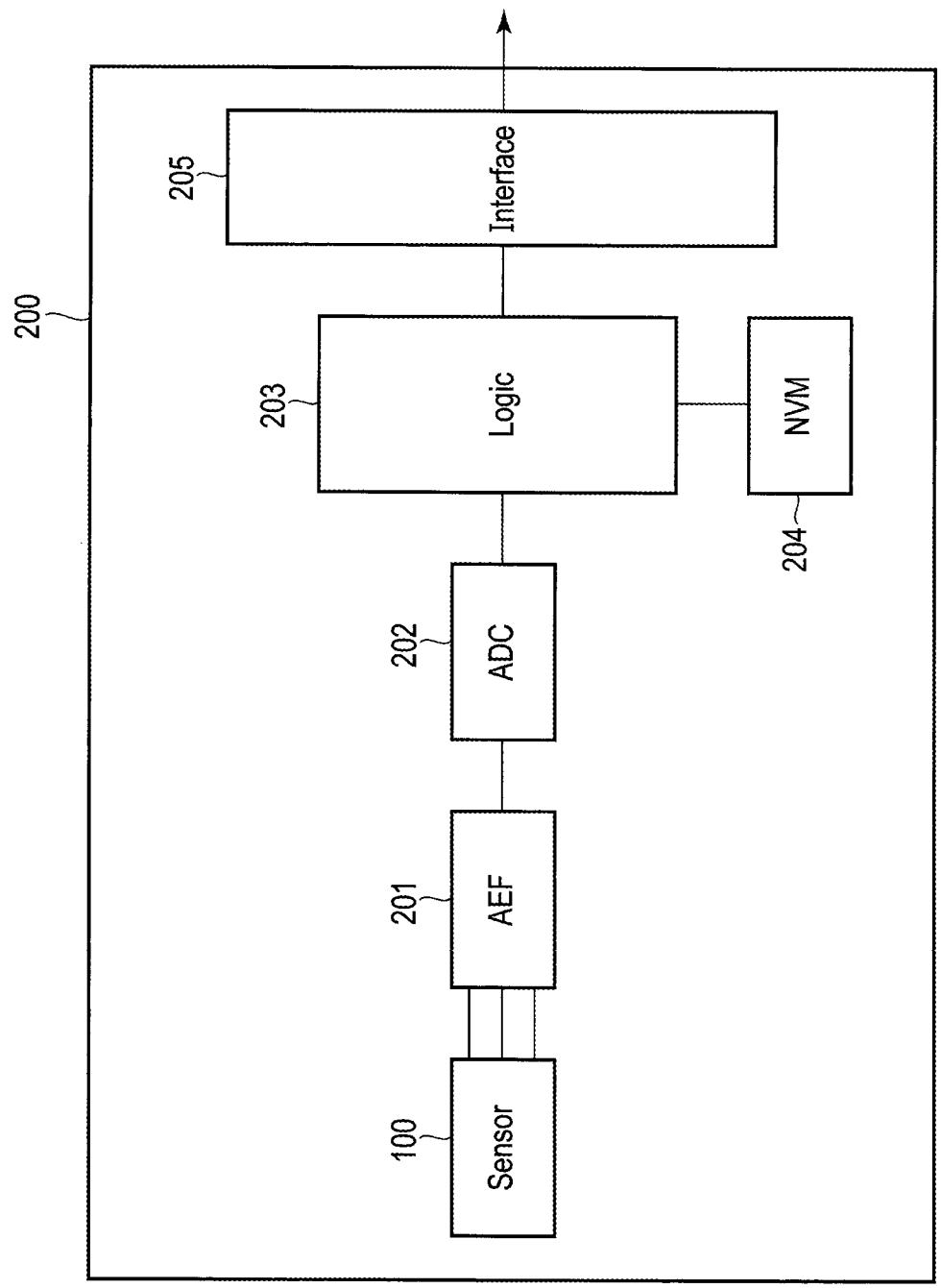
F I G. 13

HYDROGEN SENSOR, HYDROGEN DETECTING METHOD, AND NON-TRANSITORY COMPUTER-READABLE STORAGE MEDIUM

CROSS-REFERENCE TO RELATED APPLICATIONS

This application is based upon and claims the benefit of priority from Japanese Patent Application No. 2018-168890, filed Sep. 10, 2018, the entire contents of which are incorporated herein by reference.

FIELD

Embodiments described herein relate generally to a hydrogen sensor, a hydrogen detecting method, and a non-transitory computer-readable storage medium.

BACKGROUND

Various hydrogen sensors are proposed. As one of the hydrogen sensors, a capacitive type hydrogen sensor formed by using micro-electromechanical systems (MEMS) is known. Performance of this type of hydrogen sensor is expected to be improved.

BRIEF DESCRIPTION OF THE DRAWINGS

FIG. 1 is a block diagram that shows a basic structure of a hydrogen sensor according to a first embodiment.

FIG. 6 is a block diagram that shows a basic structure of a hydrogen sensor according to a second embodiment.

FIG. 10 is a table that shows relations between gas species and $\Delta C$, $\Delta R$, and $\Delta V$.

FIG. 13 is a diagram for explanation of a non-transitory computer-readable storage medium according to a fifth embodiment.

DETAILED DESCRIPTION

Figure 2A:
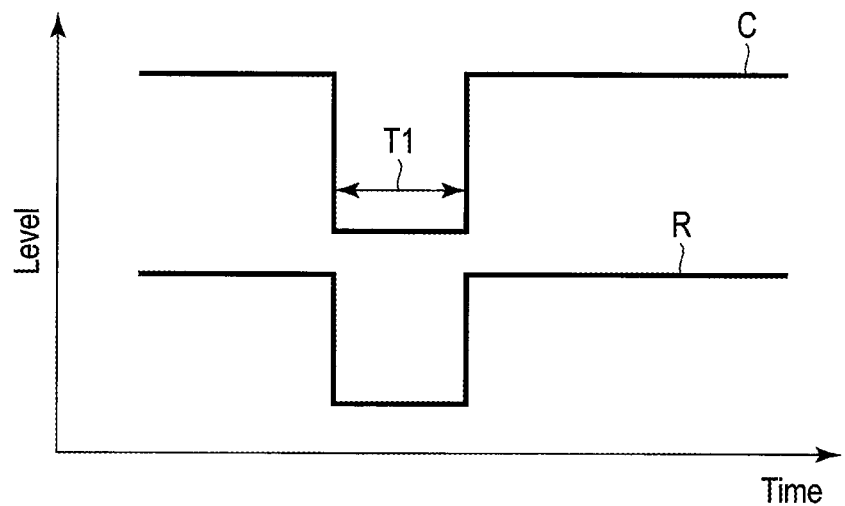
FIGS. 2A and 2B are diagrams that show relations between temporal variation of a capacitance value and temporal variation of a heater resistance value in a case where detected gas contains a substance other than hydrogen.

In general, according to one embodiment, a hydrogen sensor is disclosed. The hydrogen sensor includes a capacitor, a gas detector, a heater, and a determiner. The capacitor includes a deformable member that deforms by absorbing or adsorbing hydrogen and varies a capacitance value corresponding to a deformation of the deformable member. The gas detector detects gas based on a capacitance value of the capacitor. The heater heats the deformable member. The determiner determines whether gas detected by the gas detector contains a substance other than hydrogen or not, wherein the gas detector detects the gas during a heating period during which the heater heats the deformable member.

Embodiments will be described hereinafter with reference to the accompanying drawings. The drawings are schematic or conceptual drawings, and dimensions and ratios are not necessarily the same as those in reality. Further, in the drawings, the same reference symbols (including those having different subscripts) denote the same or corresponding parts, and overlapping explanations thereof will be made as necessary. In addition, as used in the description and the appended claims, what is expressed by a singular form shall include the meaning of "more than one".

First Embodiment

FIG. 1 is a block diagram that shows a basic structure of a hydrogen sensor 100 according to a first embodiment.

The hydrogen sensor 100 of the present embodiment includes a MEMS capacitor (capacitor) 101, a capacitance-value measuring unit (first measuring circuit) 102, a gas detecting unit (gas detector) 103, a heater controlling unit 104, a heater 105, a resistance-value measuring unit (second measuring circuit) 106, and a determining unit (determiner) 107.

The MEMS capacitor 101 includes a hydrogen occlusion layer (not shown) that deforms by absorbing or adsorbing hydrogen, and varies a capacitance value corresponding to a deformation of the hydrogen occlusion layer. A concrete structure of the MEMS capacitor 101 will be described below.

The capacitance-value measuring unit 102 measures a capacitance value of the MEMS capacitor 101 during a heating period of the hydrogen occlusion layer by the heater 105, and measures temporal variation of the capacitance value. The gas detecting unit 103 detects gas based on measurement results of the capacitance-value measuring unit 102. More specifically, the gas detecting unit 103 converts a capacitance value into a gas concentration. If the gas concentration exceeds a predetermined value, the gas detecting unit 103 detects gas.

The heater 105 efficiently heats the hydrogen occlusion layer of the MEMS capacitor 101. In the present embodiment, the heater 105 includes a conductor, such as Ti, TiN, Al, Ni, Cu, Pd, Pt, Pd—Ni, or the like. The heater 105 heats the hydrogen occlusion layer by utilizing heat (Joule's heat) generated by electric current passing through the conductor. The heater controlling unit 104 may control on/off of the heater 105 and a temperature of the heater 105 (heater temperature).

The resistance-value measuring unit 106 measures a resistance value of the conductor in the heater 105 during the heating period, and measures temporal variation of the resistance value. The determining unit 107 determines whether gas detected by the gas detecting unit 103 (detected gas) contains a substance other than hydrogen (a non-target substance) or not based on temporal variation of a capacitance value measured by the capacitance-value measuring unit 102 and temporal variation of a resistance value measured by the resistance-value measuring unit 106. This determination is performed as described below.

Figure 2B:
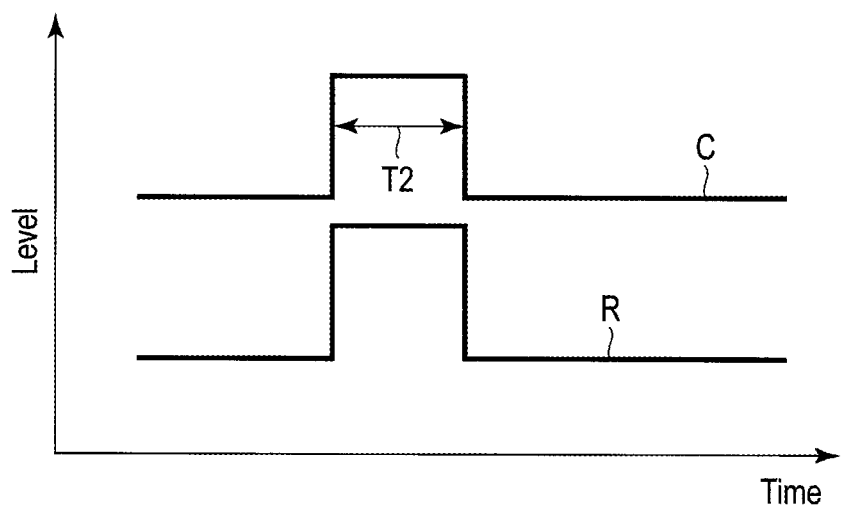

Intensive research of the present inventor shows that if detected gas contains methane ($CH_4$) as a non-target substance, a period T1 in which a decrease in a capacitance value C and a decrease in a resistance value R occur simultaneously exists in the heating period, as shown in FIG. 2A, for example. Further, the intensive research of the present inventor shows that if detected gas contains propane ($C_3H_8$) as a non-target substance, a period T2 in which an increase in a capacitance value C and an increase in a resistance value R occur simultaneously exists in the heating period, as shown in FIG. 2B, for example.

Figure 3:
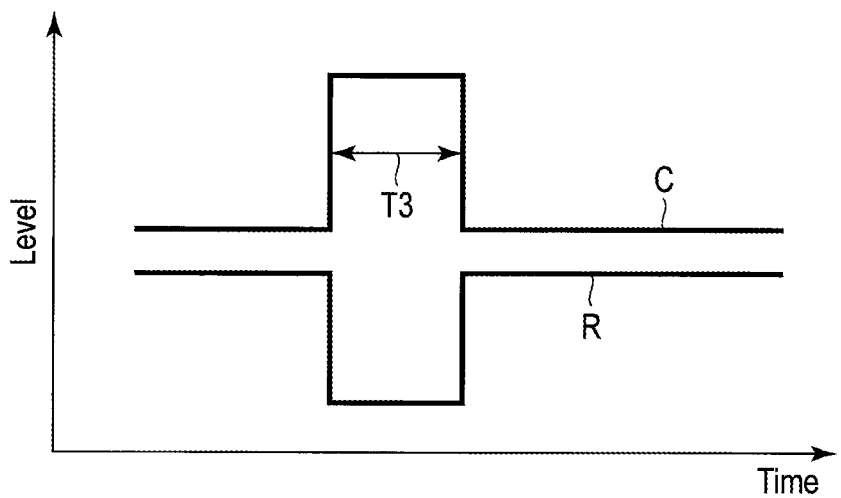
FIG. 3 is a diagram that shows a relation between temporal variation of a capacitance value and temporal variation of a heater resistance value in a case where detected gas contains hydrogen.

Moreover, the intensive research of the present inventor shows that if detected gas contains hydrogen and does not contain the non-target substance, a period T3 in which an increase in a capacitance value C and a decrease in a resistance value R occur simultaneously exists in the heating period, as shown in FIG. 3, for example.

Figure 4:
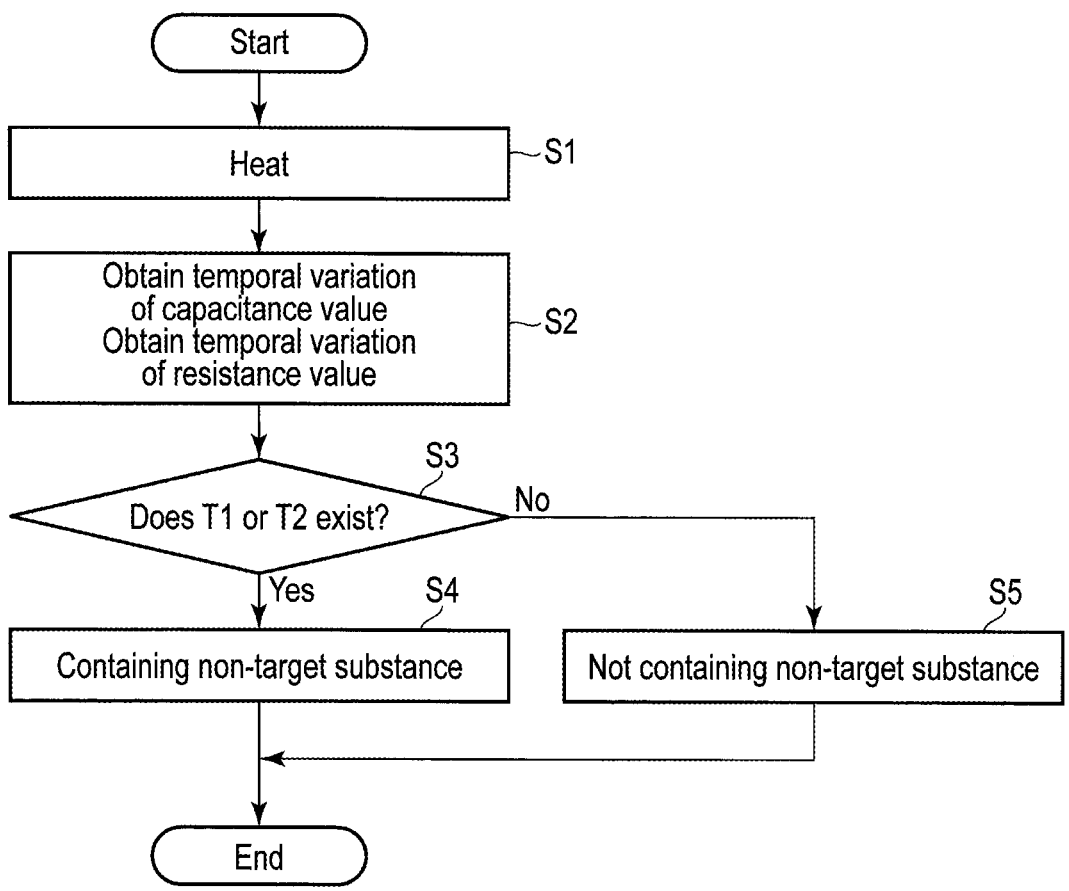
FIG. 4 is a flowchart that shows an example of a hydrogen detecting method according to the first embodiment.

FIG. 4 is a flowchart that shows an example of a hydrogen detecting method according to the present embodiment based on the above new findings.

First, the hydrogen occlusion layer of the MEMS capacitor 101 is heated by the heater 105 (step S1).

Next, temporal variation of a capacitance value during the heating period is measured by the capacitance-value measuring unit 102, and temporal variation of a resistance value during the heating period is measured by the resistance-value measuring unit 106 (step S2).

Next, the determining unit 107 determines whether the period T1 or the period T2 exists or not based on the temporal variation of the capacitance value and the temporal variation of the resistance value (step S3).

If the period T1 or the period T2 exists (Yes), the determining unit 107 determines that detected gas contains the non-target substance (step S4).

If the period T1 and the period T2 do not exist (No), the determining unit 107 determines that detected gas does not contain the non-target substance (step S5).

Note that, a step that determines whether the period T3 exists or not may be added after step S4. In this case, if the period T3 exists, the determining unit 107 determines that the detected gas contains hydrogen and the non-target substance. If the period T3 does not exist, the determining unit 107 determines that the detected gas contains the non-target substance and does not contain hydrogen.

Further, a step that determines whether the period T3 exists or not may be added after step S5. In this case, if the period T3 exists, the determining unit 107 determines that the detected gas contains hydrogen and does not contain the non-target substance. In addition, if the period T3 does not exist, the determining unit 107 determines that the detected gas does not contain hydrogen and the non-target substance.

As described above, since it is determined according to the present embodiment whether detected gas contains the non-target substance or not, the hydrogen sensor 100 that has high hydrogen selectivity and the hydrogen detecting method are provided.

Figure 5:
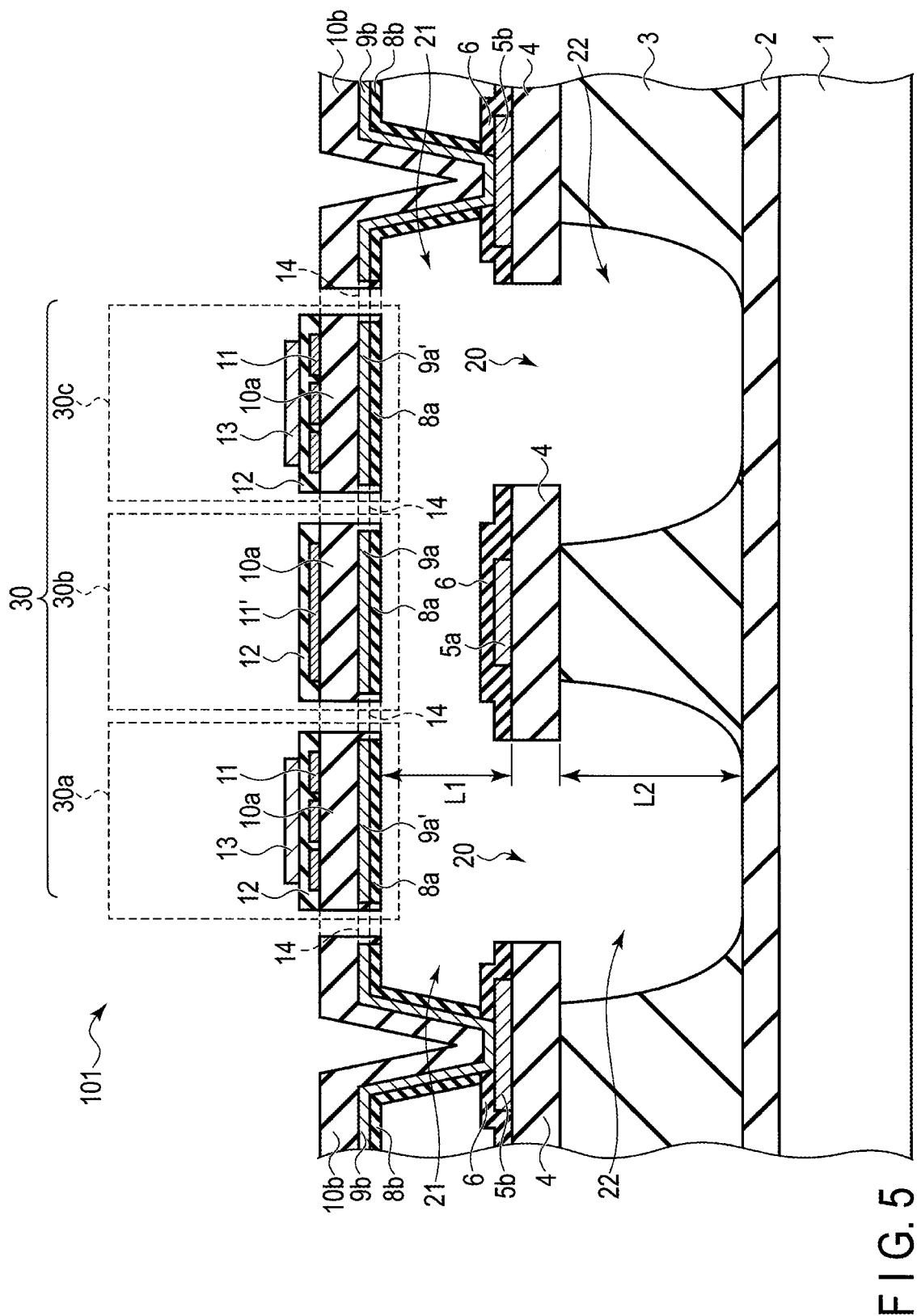
FIG. 5 is a cross-sectional view that shows an example of a concrete structure of a MEMS capacitor of the hydrogen sensor according to the first embodiment.

FIG. 5 is a cross-sectional view that shows an example of a concrete structure of the MEMS capacitor 101.

In FIG. 5, reference numeral 1 indicates a silicon substrate (substrate area), and an insulating layer (substrate area) 2 and an insulating layer (substrate area) 3 are successively disposed on the silicon substrate 1.

A material of the insulating layer 2 is different from a material of the insulating layer 3. For example, if a manufacturing process that includes ashing (dry etching) that removes the insulating layer 2 and the insulating layer 3 by oxygen ($O_2$) is employed, materials of the insulating layers 2 and 3 are selected such that an etching rate of the insulating layer 3 is greater than an etching rate of the insulating layer 2. A material of the insulating layer 2 is silicon nitride, for example, and a material of the insulating layer 3 is polyimide, for example. The insulating layer 3 is thicker than the insulating layer 2, for example.

The insulating layer 3 includes grooves that reach the insulating layer 2, and parts of an upper surface of the insulating layer 2 are exposed. In the present embodiment, a side of the insulating layer 3 has tapered shapes that become narrower from a top to a bottom (a curve that is convex toward the bottom), as shown in the cross-sectional view of FIG. 5. A cross section of a side of the insulating layer 3 may be defined by straight lines, or may be defined by straight lines and curves. Moreover, in a Cartesian coordinate system defined by three axes that are orthogonal to each other, a side of the insulating layer 3 that defines grooves is a curved surface. The side has a negative curvature, for example. If sufficient thermal resistance is secured, the insulating layer 3 may be eliminated.

An insulating layer 4 is disposed on the insulating layer 3. A material of the insulating layer 4 is silicon nitride, for example. The insulating layer 4 includes openings 20. The insulating layer 4 and the insulating layers 2, 3 define two lower cavity areas 22. A height L2 of the lower cavity areas 22 is greater than 10 μm, for example.

A lower electrode 5a and metal layers 5b are disposed on the insulating layer 4. The metal layers 5b are used as pedestals for anchors 9b. The lower electrode 5a and the metal layers 5b include the same conductive material, such as aluminum (Al), titanium (Ti), or titanium nitride (TiN).

An insulating layer 6 is disposed on the insulating layer 4 and on the lower electrode 5a that is on the insulating layer 4. Similarly, the insulating layer 6 is disposed on the insulating layer 4 and on each metal layer 5b that is on the insulating layer 4. A material of the insulating layers 6 is silicon nitride, for example.

A movable structure 30 is disposed above the lower electrode 5a. The movable structure 30 includes a hydrogen actuator 30a, an upper-electrode portion 30b, and a hydrogen actuator 30c. The upper-electrode portion 30b is disposed between the hydrogen actuators 30a and 30c. One end of the upper-electrode portion 30b is connected to the hydrogen actuator 30a through a spring portion 14. The other end of the upper-electrode portion 30b is connected to the hydrogen actuator 30c through another spring portion 14. The upper-electrode portion 30b is connected to an external circuit that is not shown.

Under the movable structure 30 (30a, 30b, 30c), there is a cavity area (upper cavity area) 21. The upper cavity area 21 under the hydrogen actuator 30a communicates with one of the lower cavity areas 22 through one of the openings 20. Similarly, the upper cavity area 21 under the hydrogen actuator 30c communicates with the other lower cavity area 22 through the other opening 20.

The upper-electrode portion 30b includes an insulating layer 8a, an upper electrode 9a, an insulating layer 10a, a conductive layer (dummy metal) 11', and an insulating layer 12.

The upper electrode 9a is disposed on the insulating layer 8a and is opposite the lower electrode 5a. The upper electrode 9a and the lower electrode 5a are two capacitor electrodes that constitute the MEMS capacitor 101. A material of the upper electrode 9a includes TiN, for example. A material of the upper electrode 9a may include other conductive materials, such as Ti, instead of TiN.

In the upper-electrode portion 30b, the insulating layer 10a is disposed on the insulating layer 8a to cover the upper electrode 9a. The conductive layer 11' is disposed on the insulating layer 10a. The conductive layer 11' is disposed to restrict warp of the insulating layer 10a due to residual stress. For the above purpose, a shape and dimensions of the conductive layer 11' are the same as those of the upper electrode 9a, for example. A material of the conductive layer 11' is Ti, TiN, Ni, Cu, Pd, Pt, or Pd—Ni, for example. The conductive layer 11' is not connected to a power source (not shown), and does not function as a heater.

In the upper-electrode portion 30b, the insulating layer 12 is disposed on the insulating layer 10a to cover the conductive layer 11'. A material of the insulating layer 10a includes silicon nitride, for example.

Each of the hydrogen actuators 30a and 30c includes an insulating layer 8a, a dummy electrode 9a', an insulating layer 10a, a heater 11, an insulating layer 12, and a hydrogen occlusion layer 13.

The dummy electrode 9a' is disposed on the insulating layer 8a. A shape of the dummy electrode 9a' is plate-like or mesh-like, for example. Since the lower electrode 5a is not disposed under the dummy electrode 9a', the dummy electrode 9a' does not function as an upper electrode of the MEMS capacitor 101.

In each of the hydrogen actuators 30a and 30c, the insulating layer 10a is disposed on the insulating layer 8a to cover the dummy electrode 9a'. The heater 11 is disposed on the insulating layer 10a.

A material of the heater 11 may be the same as or different from that of the conductive layer 11'. The heater 11 is connected to the power source (not shown).

In each of the hydrogen actuators 30a and 30c, the insulating layer 12 is disposed on the insulating layer 10a to cover the heater 11. As a result, the heater 11 is covered by the insulating layer 10a and the insulating layer 12. The insulating layer 10a and the insulating layer 12 constitute a heat insulating structure for the heater 11.

The hydrogen occlusion layer 13 is disposed on the insulating layer 12. The hydrogen occlusion layer 13 includes palladium (Pd), an alloy containing palladium (Pd), an alloy containing Pd in which copper (Cu) and silicon (Si) are added, an alloy containing titanium (Ti), an alloy containing lanthanum (La), or metallic glass, for example. The metallic glass includes the above metal (Pd, Ti, or La) or an alloy of the above metal (Pd, Ti, or La), for example.

The hydrogen occlusion layer 13 expands (increases a volume thereof) by absorbing or adsorbing (accumulating) hydrogen. If the hydrogen occlusion layer 13 expands, the hydrogen actuators 30a and 30c deforms, and a position of the upper-electrode portion 30b is displaced upward or downward. As a result, a distance between the lower electrode 5a and the upper electrode 9a varies.

Since an expansion amount of the hydrogen occlusion layer 13 varies corresponding to an absorbed-hydrogen volume or an adsorbed-hydrogen volume, the distance between the lower electrode 5a and the upper electrode 9a varies corresponding to the absorbed-hydrogen volume or the adsorbed-hydrogen volume. As a result, a capacitance value of the MEMS capacitor 101 varies corresponding to the absorbed-hydrogen volume or the adsorbed-hydrogen volume of the hydrogen occlusion layer 13.

One end of the hydrogen actuator 30a is connected to one of the anchors 9b through a spring portion 14. An insulating layer 8b is disposed on a bottom side of each anchor 9b, and an insulating layer 10b is disposed on a top side of each anchor 9b. The hydrogen actuator 30c is similarly constituted.

To prevent electric power consumption of the heater 11 from increasing, heat escaping from the hydrogen actuators 30a and 30c each of which includes the heater 11 may be decreased. For that purpose, a thermal resistance of the upper cavity area 21 is increased by increasing the upper cavity area 21, for example. To increase the upper cavity area 21, a height L1 of the upper cavity area 21 needs to be increased, for example. The increased height L1 increases the distance between the lower electrode 5a and the upper electrode 9a. The increased distance decreases capacitance of the MEMS capacitor. As a result, detection sensitivity for hydrogen concentration decreases.

In the present embodiment, therefore, the lower cavity areas 22 are formed under the upper cavity area 21. The upper cavity area 21 communicates with the lower cavity areas 22 through the openings 20, and the upper cavity area 21 is connected to the lower cavity areas 22 in series. Consequently, a total thermal resistance of a thermal resistance of the upper cavity area 21 and a thermal resistance of the lower cavity areas 22 is a sum of these two thermal resistances. Therefore, since thermal resistances of the cavity areas under the hydrogen actuators 30a and 30c are increased, electric power consumption of the heater 11 is prevented from increasing while detection sensitivity for hydrogen concentration is increased.

Note that, the height L1 of the upper cavity area 21 is smaller than the height L2 (L1<L2) in FIG. 5, L1≥L2 may be possible if a sufficient thermal resistance is secured. In addition, two hydrogen actuators are shown in FIG. 5 as an example, the number of the hydrogen actuators may be one or three or more.

Second Embodiment

FIG. 6 is a block diagram that shows a basic structure of a hydrogen sensor 100 according to a second embodiment.

The hydrogen sensor 100 of the present embodiment includes a thermally conductive type gas sensor 110, and an output-value measuring unit (third measuring circuit) 111 that measures an output value from the thermally conductive type gas sensor 110.

The thermally conductive type gas sensor 110 includes a sensor element configured to come into contact with predetermined gases, a reference element disposed in a structure (a sealed structure) which does not come into contact with the predetermined gases, a heater that heats the sensor element and the reference element, and a bridge circuit that includes a variable resistor.

If the predetermined gases come into contact with the sensor element while the heater heats the sensor element and the reference element, a state of heat dissipation is changed by a thermal conductivity inherent in the gases, and a temperature of the sensor element varies. A resistance value of the heater varies by the temperature variation. On the other hand, since the reference element does not come into contact with the predetermined gases, a temperature (resistance value) of the reference element does not vary.

Here, the bridge circuit has been put in balance by adjusting the variable resistor in an atmosphere without the predetermined gases. Therefore, if the predetermined gases exist, a resistance value of the sensor element increases, and the bridge circuit is out of balance. The bridge circuit measures variation of a resistance value of the sensor element as a voltage value (sensor output value).

The output-value measuring unit 111 measures temporal variation of a resistance value of the sensor element based on an output value (voltage value) from the thermally conductive type gas sensor 110.

The present embodiment achieves the same effect as the first embodiment. Further, according to the present embodiment, a temperature of a heater 105 that heats a hydrogen occlusion layer of a MEMS capacitor 101 is set independently of a temperature of the heater in the thermally conductive type gas sensor 110. Thus, the hydrogen occlusion layer is heated at an optimum temperature, and the sensor element in the thermally conductive type gas sensor 110 is also heated at an optimum temperature. As a result, performance of the hydrogen sensor 100 (e.g., detection accuracy and gas selectivity) is improved.

Figure 7:
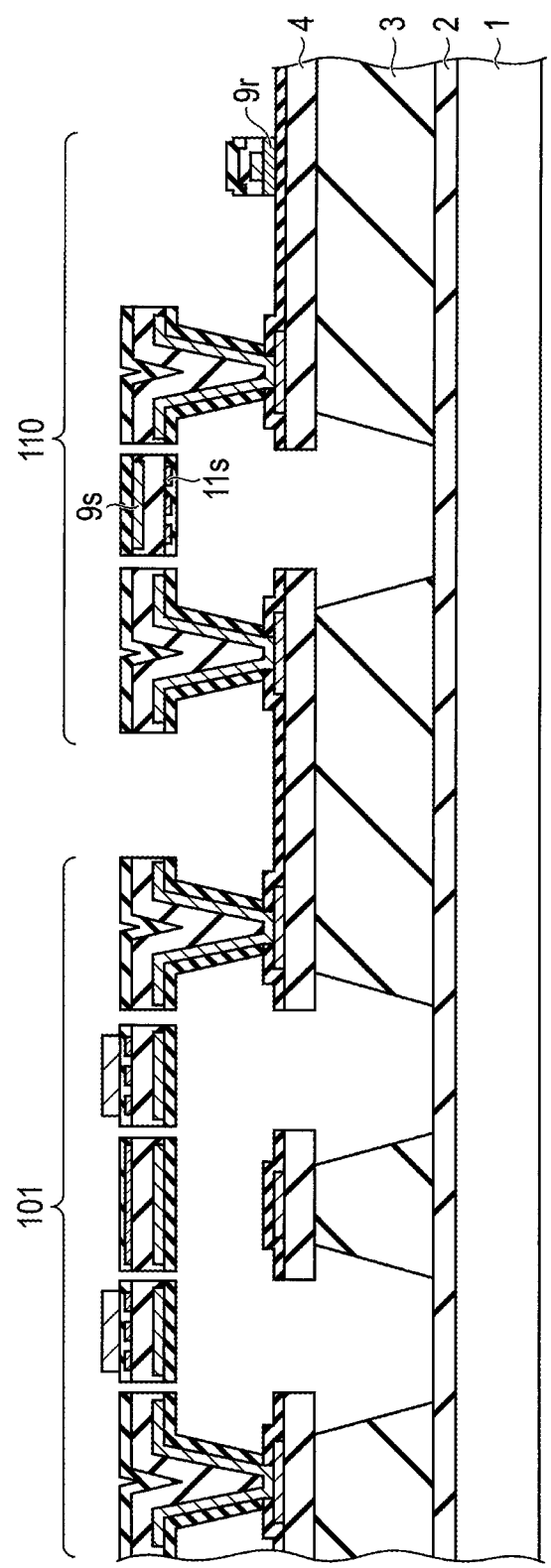
FIG. 7 is a cross-sectional view that shows an example in which a MEMS capacitor and a thermally conductive type gas sensor of the hydrogen sensor according to the second embodiment are disposed.

FIG. 7 is a cross-sectional view that shows an example of implementation of the MEMS capacitor 101 and the thermally conductive type gas sensor 110 of the hydrogen sensor according to the present embodiment. The thermally conductive type gas sensor 110 is disposed adjacently to the MEMS capacitor 101. The thermally conductive type gas sensor 110 includes a temperature measuring resistor 9s as the sensor element, a heater 11s that heats the temperature measuring resistor 9s, and a temperature measuring resistor 9r as the reference element. The temperature measuring resistor 9s is exposed to come into contact with gases, and the temperature measuring resistor 9r is disposed in the sealed structure.

Figure 8:
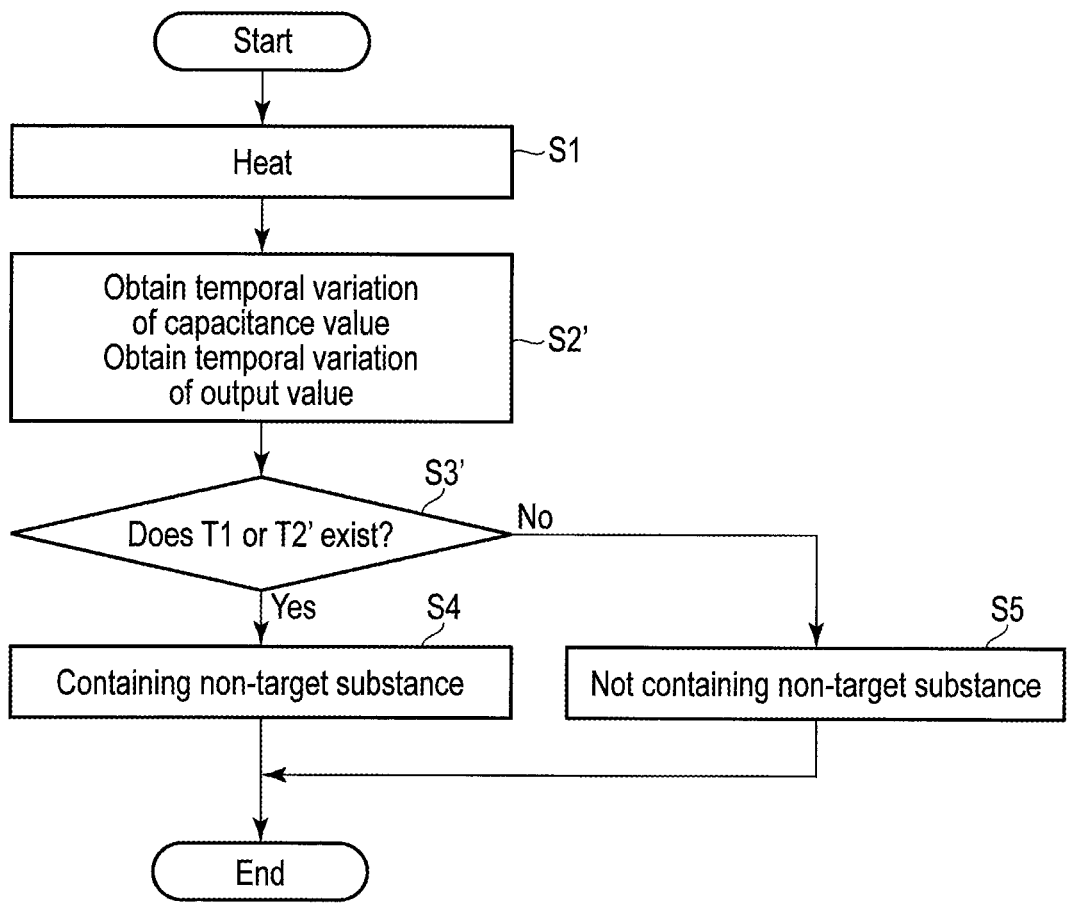
FIG. 8 is a flowchart that shows an example of a hydrogen detecting method according to the second embodiment.

FIG. 8 is a flowchart that shows an example of a hydrogen detecting method of the present embodiment.

First, the hydrogen occlusion layer of the MEMS capacitor 101 is heated (step S1).

Next, temporal variation of a capacitance value during the heating period is measured by using the capacitance-value measuring unit 102, and temporal variation of an output value (resistance value of the temperature measuring resistor 9s) from the thermally conductive type gas sensor 110 during the heating period is measured by using the output-value measuring unit 111 (step S2').

Next, the determining unit 107 determines whether the period T1 or a period T2' exists or not based on the temporal variation of the capacitance value and the temporal variation of the output value (step S3'). The period T2' is a period in which an increase in the capacitance value and an increase in the output value (resistance value of the temperature measuring resistor 9s) occur simultaneously in the heating period.

If the period T1 or the period T2' exists (Yes), the determining unit 107 determines that detected gas contains the non-target substance (step S4).

If the period T1 and the period T2 do not exist (No), the determining unit 107 determines that detected gas does not contain the non-target substance (step S5).

Note that, a step that determines whether the period T3 exists or not may be added after step S4 or step S5, similarly as the first embodiment.

Third Embodiment

Figure 9:
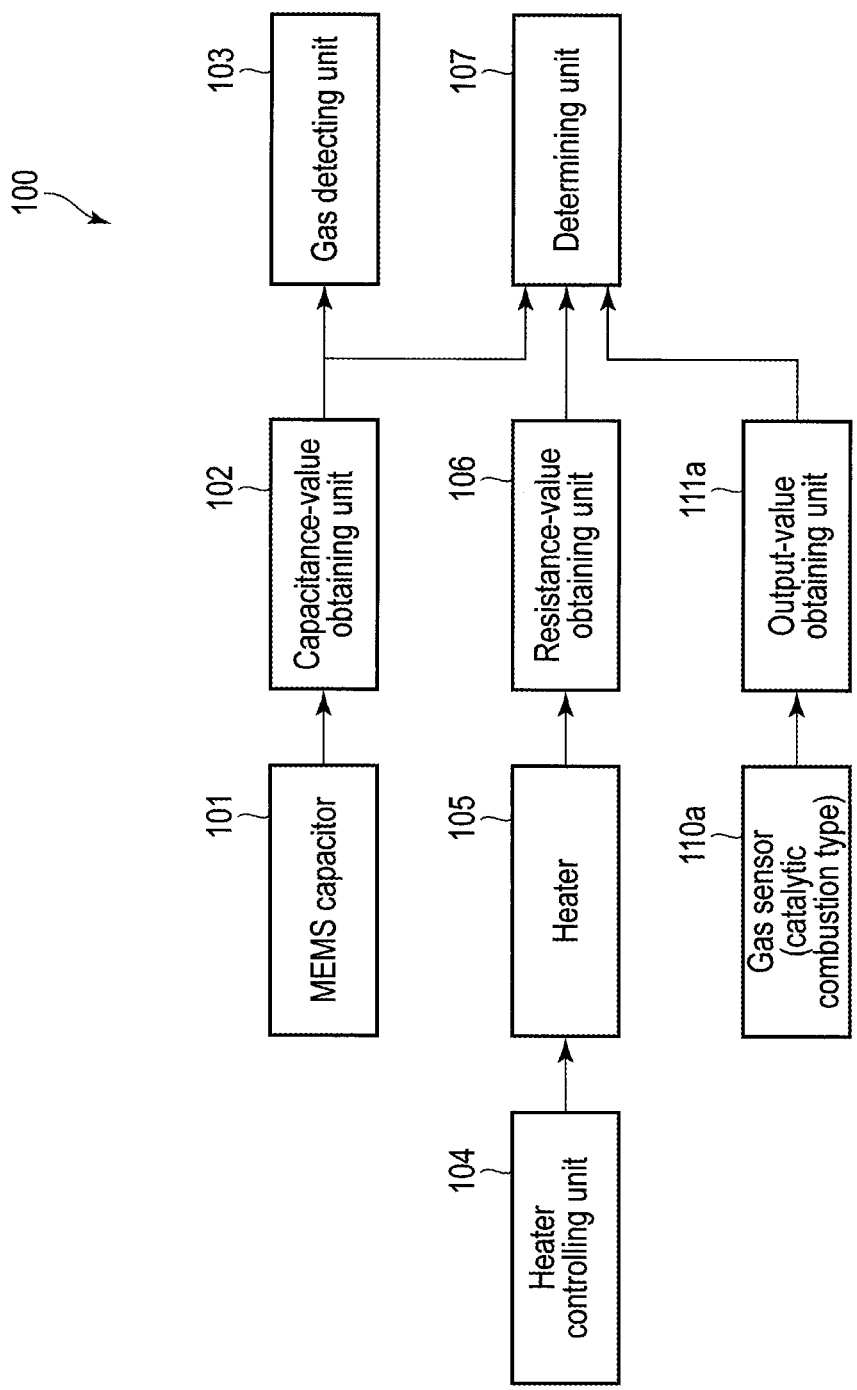
FIG. 9 is a block diagram that shows a basic structure of a hydrogen sensor according to a third embodiment.

FIG. 9 is a block diagram that shows a basic structure of a hydrogen sensor 100 according to a third embodiment.

The hydrogen sensor 100 of the present embodiment includes a catalytic combustion type gas sensor 110a, and an output-value measuring unit 111a that measures an output value from the catalytic combustion type gas sensor 110a.

The catalytic combustion type gas sensor 110a includes a sensor element that includes a catalyst layer that responds to predetermined gases, a reference element that does not include a catalyst layer that responds to the predetermined gases, a heater that heats the sensor element and the reference element, and a bridge circuit that includes a variable resistor.

If the predetermined gases exist while the heater heats the sensor element and the reference element, the gases responds to the catalyst layer of the sensor element and combust, and a temperature of the sensor element increases. As a result, a resistance value of the sensor element increases. On the other hand, since the reference element does not include a catalyst layer, the reference element does not respond to the predetermined gases, and a temperature (resistance value) of the reference element does not vary.

Here, the bridge circuit has been put in balance by adjusting the variable resistor in an atmosphere without the predetermined gases. Therefore, if the predetermined gases exist, a resistance value of the sensor element increases, and the bridge circuit is out of balance. The bridge circuit measures variation of a resistance value of the sensor element as a voltage value.

The output-value measuring unit 111a measures temporal variation of a resistance value of the sensor element based on an output value (voltage value) from the catalytic combustion type gas sensor 110a.

The determining unit 107 determines whether detected gas contains the non-target substance or not based on an output value from a capacitance-value measuring unit 102, an output value from a resistance-value measuring unit 106, and an output value from the output-value measuring unit 111a. This determination is performed as described below.

FIG. 10 is a table that shows a relation between gas species, temporal variation $\Delta C$ of an output value from the capacitance-value measuring unit 102, temporal variation $\Delta R$ of an output value from the resistance-value measuring unit 106, and temporal variation $\Delta V$ of an output value from the output-value measuring unit 111a. In FIG. 10, a "+" means that temporal variation of an output value is positive, a "−" means that temporal variation of an output value is negative, and a "0" means that temporal variation of an output value is zero or substantially zero.

As shown in FIG. 10, it is determined that combinations other than a combination of positive temporal variation $\Delta C$, negative temporal variation $\Delta R$, and positive temporal variation $\Delta V$ mean that detected gas contains the non-target substance. By using the three kinds of output values, five kinds of substances other than hydrogen can be distinguished For example, in a hydrogen detecting method of the present embodiment, steps S1 to S4 in FIG. 4 are performed while the catalytic combustion type gas sensor 110a is turned off, and then the catalytic combustion type gas sensor 110a is turned on to distinguish the five kinds of substances other than hydrogen based on temporal variation of the three kinds of output values. Since this hydrogen detecting method shortens a period during which the catalytic combustion type gas sensor 110a is on, and thus electric power consumption is prevented from increasing.

Figure 11:
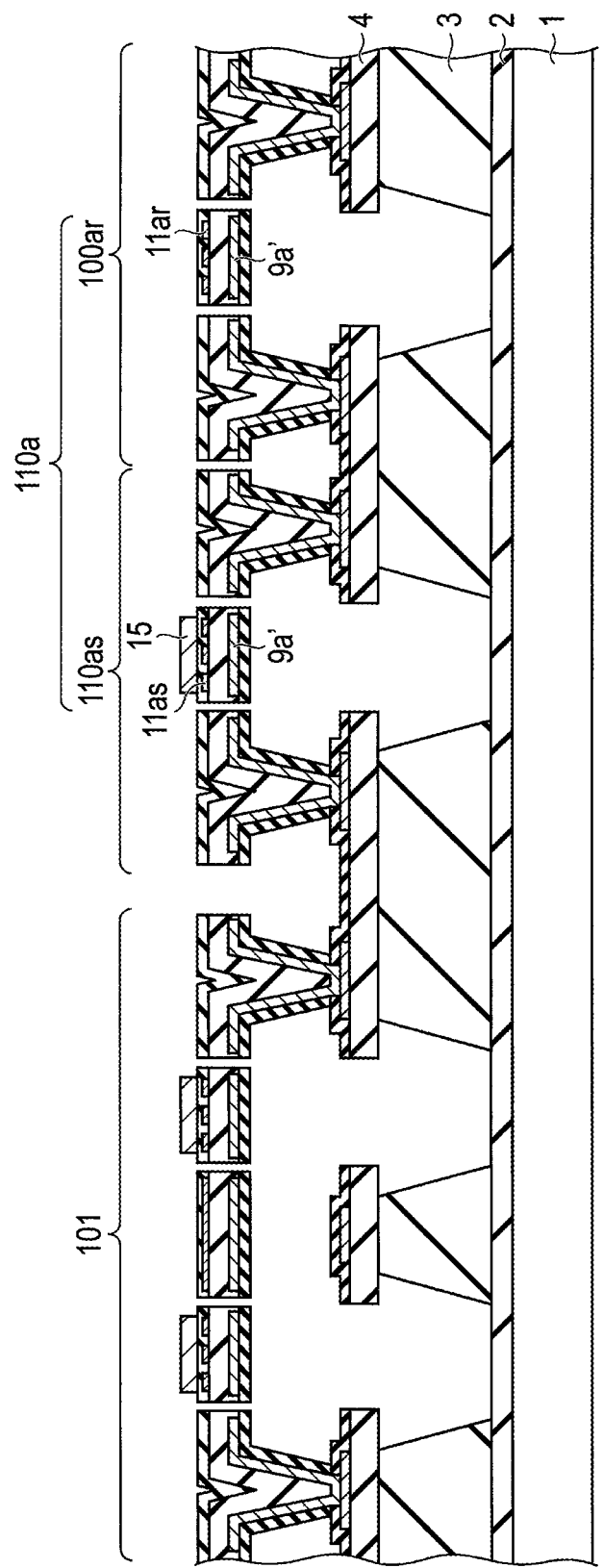
FIG. 11 is a cross-sectional view that shows an example in which a MEMS capacitor and a catalytic combustion type gas sensor of the hydrogen sensor according to the third embodiment are disposed.

FIG. 11 is a cross-sectional view that shows an example of implementation of the MEMS capacitor 101 and the catalytic combustion type gas sensor 110a of the hydrogen sensor according to the present embodiment. The catalytic combustion type gas sensor 110a is disposed adjacently to the MEMS capacitor 101. The catalytic combustion type gas sensor 110a includes a sensor element 110as and a reference element 110ar. The sensor element 110as includes a heater 11as and a catalyst layer 15. The heater 11as heats the catalyst layer 15. A material of the catalyst layer 15 is Pd, PdCuSi, a Pd alloy, Pt, or a Pt alloy, for example. The reference element 110*ar* has a similar structure as the sensor element 110*as* except that the catalyst layer is eliminated. Reference numeral 11*ar* indicates a heater for the reference element 110*ar*.

Fourth Embodiment

Figure 12:
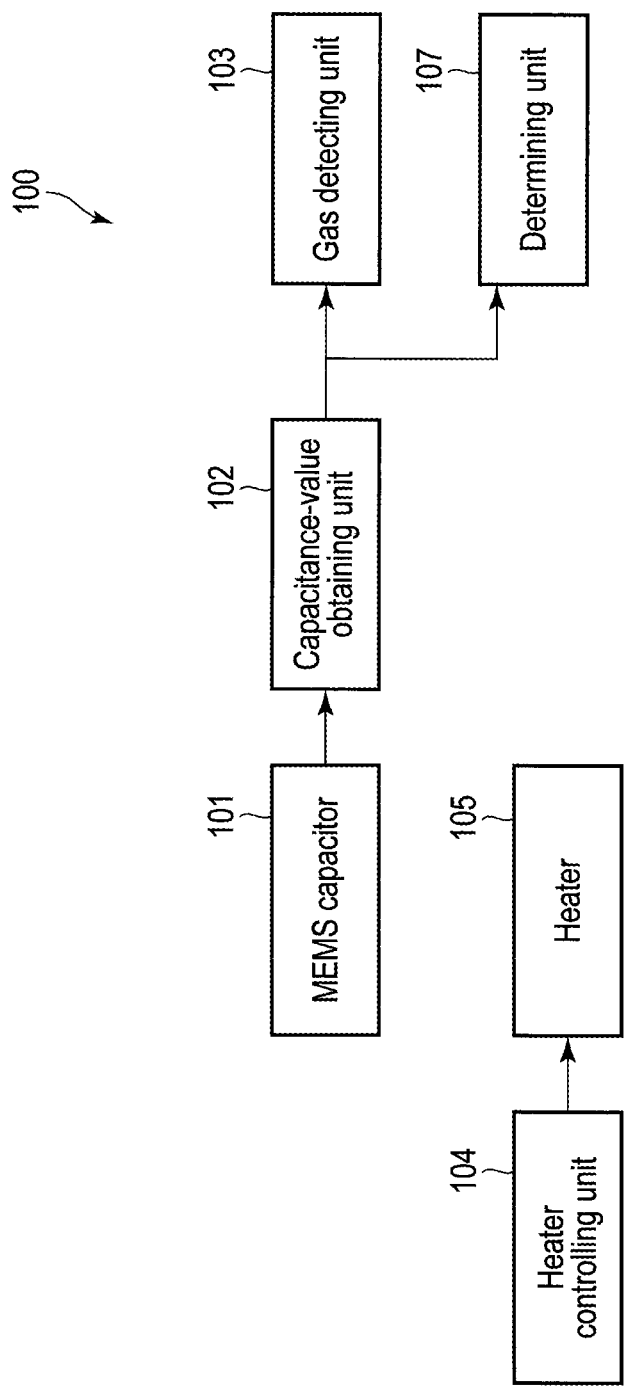
FIG. 12 is a block diagram that shows a basic structure of a hydrogen sensor according to a fourth embodiment.

FIG. 12 is a block diagram that shows a basic structure of a hydrogen sensor 100 according to a fourth embodiment.

Intensive research of the present inventor shows that if detected gas contains the non-target substance, a capacitance value of a MEMS capacitor 101 during a period during which a heater 105 is on is different from a capacitance value of the MEMS capacitor 101 during a period during which the heater 105 is off (reference capacitance value).

Thus, the hydrogen sensor 100 of the present embodiment determines whether detected gas contains the non-target substance or not by comparing a capacitance value of the MEMS capacitor 101 during a period during which the heater 105 is on and a reference capacitance value by means of a determining unit 107.

Fifth Embodiment

The hydrogen detecting methods of the above embodiments can be implemented as a non-volatile memory 204 of a detection device 200 as shown in FIG. 13. The detection device further includes a hydrogen sensor 100, an analog front-end (AFE) 201, an digital-analog converter (ADC) 202, a logic circuit 203, and an interface circuit 205.

The output (along signal) of the hydrogen sensor 100 is input into the ADC 202 through the AFE 201. The ADC 202 converts the along signal into a digital signal. The digital signal is input into the logic circuit 203. The non-volatile memory 204 is a non-transitory computer-readable storage medium, and includes instructions 205 according to the hydrogen detecting method of the embodiment that are readable and executed by the logic circuit 203. The instructions 205 cause the logic circuit 203 to execute steps S1 to S5 (instructions) of FIG. 4 or steps S1 to S5 (instructions) of FIG. 8.

The logic circuit 203, which executes the instructions, outputs a signal indicating presence or absence of hydrogen. The output signal is input into the interface circuit 205, and thus outputting the signal outside the detection device.

Note that, in the first to fifth embodiments, the determining unit determines whether gas detected by the gas detecting unit contains a substance other than hydrogen or not based on temporal variation of the capacitance value of the MEMS capacitor during the heating period, and temporal variation of the resistance value during the heating period. Instead, the determining unit may determine whether gas detected by the gas detecting unit contains a substance other than hydrogen or not based on the capacitance value of the MEMS capacitor during the heating period, and the resistance value during the heating period.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A hydrogen sensor comprising:
a capacitor including a deformable member configured to deform by absorbing or adsorbing hydrogen and configured to vary a capacitance value corresponding to a deformation of the deformable member;
a gas detector configured to detect gas based on a capacitance value of the capacitor;
a thermally conductive type gas sensor;
a heater configured to heat the deformable member; and
a determiner configured to determine whether gas detected by the gas detector contains a substance other than hydrogen or not, wherein the gas detector detects the gas during a heating period during which the heater heats the deformable member, and wherein the determiner determines whether gas detected by the gas detector contains the substance or not based on temporal variation of a capacitance value of the capacitor during the heating period, and temporal variation of an output value from the thermally conductive type gas sensor during the heating period.

2. The hydrogen sensor according to claim 1, wherein:
the heater includes a conductor, and
the determiner determines whether gas detected by the gas detector contains the substance or not based on temporal variation of a resistance value of the conductor during the heating period.

3. The hydrogen sensor according to claim 2, wherein the determiner determines whether at least one of a first period in which a decrease in the capacitance value and a decrease in the resistance value occur simultaneously in the heating period and a second period in which an increase in the capacitance value and an increase in the resistance value occur simultaneously in the heating period exists or not, and
when at least one of the first period and the second period exists, the determiner determines that the detected gas contains the substance.

4. The hydrogen sensor according to claim 2, further comprising:
a first measuring circuit configured to measure the temporal variation of the capacitance value; and
a second measuring circuit configured to measure the temporal variation of the resistance value.

5. The hydrogen sensor according to claim 1, wherein the determiner determines whether at least one of a first period in which a decrease in the capacitance value and a decrease in the output value occur simultaneously in the heating period and a second period in which an increase in the capacitance value and an increase in the output value occur simultaneously in the heating period exists or not; and
when at least one of the first period and the second period exists, the determiner determines that the detected gas contains the substance.

6. The hydrogen sensor according to claim 1, further comprising:
a first measuring circuit configured to measure the temporal variation of the capacitance value; and
a third measuring circuit configured to measure the temporal variation of the output value.

7. The hydrogen sensor according to claim 1, wherein the determiner determines whether gas detected by the gas detector contains the substance or not based on a capacitance value of the capacitor during the heating period during which the heater heats the deformable member, and a capacitance value of the capacitor during a non-heating period during which the heater does not heat the deformable member.

8. The hydrogen sensor according to claim 1, wherein the determiner determines whether gas detected by the gas detector contains hydrogen or not.

9. The hydrogen sensor according to claim 1, wherein the capacitor includes a MEMS capacitor.

10. The hydrogen sensor according to claim 9, wherein the MEMS capacitor is disposed on a substrate area that includes a cavity area.

11. The hydrogen sensor according to claim 1, wherein the substance other than hydrogen is methane, propane, $CO_2$ or He.

12. The hydrogen sensor according to claim 1, wherein the capacitor includes a first electrode and a second electrode disposed away from the first electrode, and a distance between the first electrode and the second electrode varies corresponding to the deformation of the deformable member.

13. The hydrogen sensor according to claim 12, wherein the capacitor is provided on a substrate area that includes a cavity area.

14. A hydrogen detecting method that uses a hydrogen sensor which comprises a capacitor including a deformable member configured to deform by absorbing or adsorbing hydrogen, and configured to vary a capacitance value corresponding to a deformation of the deformable member; a gas detector configured to detect gas based on a capacitance value of the capacitor; a heater configured to heat the deformable member: and a thermally conductive type gas sensor,
the hydrogen detecting method comprising:
heating the deformable member by the heater; and
determining whether gas detected by the gas detector contains a substance other than hydrogen or not, wherein the gas detector detects the gas during a heating period during which the heater heats the deformable member,
wherein the determining comprises determining whether the detected gas contains the substance or not based on temporal variation of a capacitance value of the capacitor during the heating period, and temporal variation of an output value from the thermally conductive type gas sensor during the heating period.

15. The hydrogen detecting method according to claim 14, wherein:
the heater includes a conductor, and
the determining comprises determining whether the detected gas contains the substance or not based temporal variation of a resistance value of the conductor during the heating period.

16. The hydrogen detecting method according to claim 14, wherein the substance other than hydrogen is methane, propane, $CO_2$ or He.

17. The hydrogen detecting method according to claim 14, wherein the capacitor includes a first electrode and a second electrode disposed away from the first electrode, and a distance between the first electrode and the second electrode varies corresponding to the deformation of the deformable member.

18. The hydrogen detecting method according to claim 17, wherein the capacitor includes a MEMS capacitor provided on a substrate area that includes a cavity area.

19. A non-transitory computer-readable storage medium storing computer-executable instructions for a hydrogen detecting method using a hydrogen sensor which comprises a capacitor including a deformable member configured to deform by absorbing or adsorbing hydrogen and configured to vary a capacitance value corresponding to a deformation of the deformable member; a gas detector configured to detect gas based on a capacitance value of the capacitor; a heater configured to heat the deformable member; and a thermally conductive type gas sensor,
the computer-executable instructions configured to, when executed, cause a computer to perform:
heating the deformable member by the heater; and
determining whether gas detected by the gas detector contains a substance other than hydrogen or not, wherein the gas detector detects the gas during a heating period during which the heater heats the deformable member,
wherein the determining comprises determining whether the detected gas contains the substance or not based on temporal variation of a capacitance value of the capacitor during the heating period, and temporal variation of an output value from the thermally conductive type gas sensor during the heating period.

* * * * *